United States Patent
Tenerz et al.

(10) Patent No.: US 6,926,674 B2
(45) Date of Patent: Aug. 9, 2005

(54) COMBINED PRESSURE-VOLUME SENSOR AND GUIDE WIRE ASSEMBLY

(75) Inventors: Lars Tenerz, Uppsala (SE); Leif Smith, Uppsala (SE); Ola Hammarström, Lerdala (SE); Lars-Åke Brodin, Täby (SE); Håkan Elmqvist, Bromma (SE); Emil Söderqvist, Tumba (SE); Camilla Carlsson, Älvsjö (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/475,126

(22) PCT Filed: Apr. 19, 2002

(86) PCT No.: PCT/SE02/00771
§ 371 (c)(1),
(2), (4) Date: Dec. 18, 2003

(87) PCT Pub. No.: WO02/085442
PCT Pub. Date: Oct. 31, 2002

(65) Prior Publication Data
US 2004/0116816 A1 Jun. 17, 2004

Related U.S. Application Data

(60) Provisional application No. 60/284,512, filed on Apr. 19, 2001.

(51) Int. Cl.[7] .................................................. A61B 5/02
(52) U.S. Cl. ....................................... 600/486; 485/585
(58) Field of Search ................................ 600/481, 483, 600/485, 486, 488, 547, 504–507, 561, 585; 604/164.13; 607/23

(56) References Cited

U.S. PATENT DOCUMENTS

| | | | | |
|---|---|---|---|---|
| 5,324,326 A | * | 6/1994 | Lubin | 607/122 |
| 5,479,935 A | * | 1/1996 | Essen-Moller | 600/547 |
| 5,902,248 A | * | 5/1999 | Millar et al. | 600/485 |
| 5,902,624 A | | 5/1999 | Vleugels | |
| 5,938,624 A | | 8/1999 | Akerfeldt et al. | |
| 6,096,036 A | * | 8/2000 | Bowe et al. | 606/41 |
| 6,106,486 A | | 8/2000 | Tenerz et al. | |
| 6,112,115 A | | 8/2000 | Feldman et al. | |
| 6,115,624 A | * | 9/2000 | Lewis et al. | 600/376 |
| 6,142,958 A | | 11/2000 | Hammarström et al. | |
| 6,167,763 B1 | | 1/2001 | Tenerz et al. | |
| 6,615,067 B2 | * | 9/2003 | Hoek et al. | 600/381 |

FOREIGN PATENT DOCUMENTS

WO   WO 00/62851 A1   10/2000

OTHER PUBLICATIONS

Trinity College, The Biomedical Engineering Handbook, CRC Press, Inc., 1995, p. 488.*

* cited by examiner

*Primary Examiner*—Robert L. Nasser
(74) *Attorney, Agent, or Firm*—Foley & Lardner LLP

(57) ABSTRACT

The invention relates to a sensor and guide wire assembly including a pressure sensor having a plurality of terminals, the sensor being mounted in the distal end region of a core wire. It also includes two to four electrodes for conductance measurement, also provided in the distal end region. Two electrodes are electrically insulated from each other.

13 Claims, 4 Drawing Sheets

US 6,926,674 B2

COMBINED PRESSURE-VOLUME SENSOR AND GUIDE WIRE ASSEMBLY

FIELD OF THE INVENTION

The present invention relates to a guide wire for combined and simultaneous pressure and volume measurements in intravascular applications.

BACKGROUND OF THE INVENTION

The possibility of performing measurements of properties such as pressure, temperature, volume and flow within internal body organs has become increasingly important in for example diagnosis of heart diseases.

Sensor and guide wire assemblies are guide wires that have measurement sensors located at or near their distal tips. These devices are typically used in applications to measure internal properties of internal tissues and fluids such as blood pressure. Sensor and guide wire assemblies may be introduced directly into arteries, veins or other body organs either by themselves or through catheters that have been previously positioned within a patient. A sensor and guide wire assembly is disclosed in U.S. Pat. No. 6,142,958 and a pressure sensor and guide wire assembly for biological pressure measurements is disclosed in U.S. Pat. No. 6,167,763 which hereby are incorporated by reference. These sensor and guide wire assemblies typically have an outer diameter of 0.035 mm (0.014").

To increase the diagnostic value for many type of heart diseases and blood vessel alterations such as arteriosclerosis, it would be desirable to combine the pressure measurement with volumetric measurements. In the case of diagnosis of heart diseases so called "Pressure/Volume loops", PV-loops, are of particular interest. An established method of estimating the volume of internal cavities of body organs, for example the heart chamber, is by measuring the conductance.

Vessel compliance is also a measure of the status of a blood vessel, in that a soft vessel will be subject to some expansion upon an increased internal pressure, whereas a stiff vessel, indicating arteriosclerosis, would be subject to less expansion. It would be desirable to be able to measure such vessel compliance in a reliable way.

U.S. Pat. No. 6,112,115 disclose a method of producing PV-loops using a conductance catheter and a micro pressure catheter inserted in said conductance catheter. The usage of several different catheters adds complexity, and possibly discomfort for the patient.

In U.S. Pat. No. 5,902,248 (Millar) the inventors describe a catheter tip pressure transducer also including electrodes enabling conductance measurements. However, a catheter lacks the flexibility of sensor and guide wire assemblies and thus less suitable for some applications requiring a very flexible distal region. Furthermore, this patent is directed to use in animals, in particular mice.

In order to create a minimal invasive method of diagnosis it is highly desirable to also include the ability for conductance measurements in the sensor and guide wire assembly.

SUMMARY OF THE INVENTION

Thus, there exists a need for a sensor and guide wire assembly that also has the possibility of conductance measurements.

An object of the invention is therefore to provide a sensor and guide wire assembly having electrodes for enabling conductance measurements in a way that does not significantly increase the size and complexity of the assembly. This is achieved by the sensor and guide wire assembly defined in claim 1.

One advantage with such a sensor and guide wire assembly is that pressure and volume measurements can be done simultaneously with the same measurement device.

Another advantage is that the proposed sensor and guide wire assembly is equipped with the ability of conductance measurement without significantly increasing the outer diameter of the guide wire.

Still a further advantage is that the proposed combined pressure and volume guide wire assembly has a minimum complex construction and thus reducing manufacturing cost as well as reducing the risks of malfunction.

An additional advantage with the device according to the invention is that it is steerable to a desired location in the vascular system.

In one aspect of the invention the device and method is used to obtain the previously mentioned PV-loops.

In a further aspect, the device and method is used for determining vessel compliance, as discussed above, by performing pressure and conductance measurements in blood vessel.

DETAILED DESCRIPTION OF THE INVENTION

Embodiments of the invention will now be described with reference to the figures.

Figure 1:
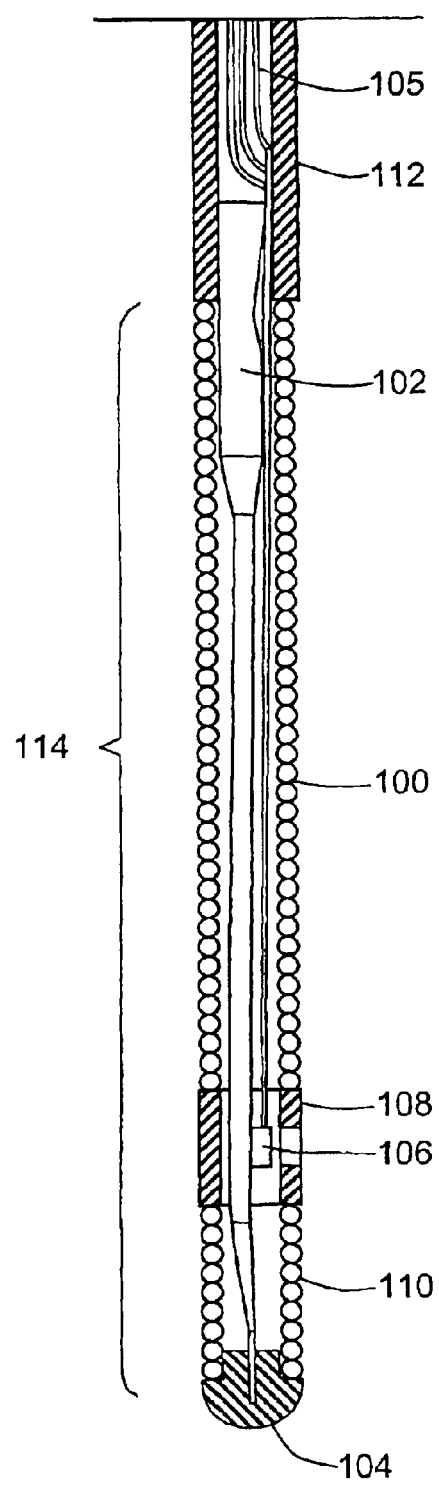
FIG. 1 shows (Prior Art) sensor and guide wire assembly in longitudinal cross section.

With references to FIG. 1 there is shown a prior art sensor and guide wire assembly, disclosed in U.S. Pat. No. 5,938,624.

The distal tip illustrated in FIG. 1 includes a first coil 100 over a tapered core wire 102. The core wire 102 is tapered to give the desired flexibility and torsional strength of the different sections of the distal tip. The distal tip is preferably finished in a rounded tip 104, which may be of solder. A pressure sensor 106 may be connected to the conductor 105, and may be positioned near the distal tip under a protective jacket 108. A second coil 110 encloses the core wire from the protective jacket 108 to the distal tip 104. The region of the sensor and guide wire assembly comprising members 100, 102, 104, 106, 108 and 110 is referred to as the distal region 114 of the guide wire. The first coil 100 and the core wire 102 are connected to a proximal tube 112. In FIG. 1 is indicated that the core wire only extends a short distances into the proximal tube 112. Alternatively the core wire can extend through the whole length of the guide wire. The sensor and guide wire assembly with described reference to FIG. 1 is only one of many embodiments of a sensor and guide wire assembly that can utilize the invention. Such alternative embodiments are described in for example U.S. Pat. Nos. 6,142,958, 6,167,763 and 6,106,486 hereby incorporated by references.

Figure 2:
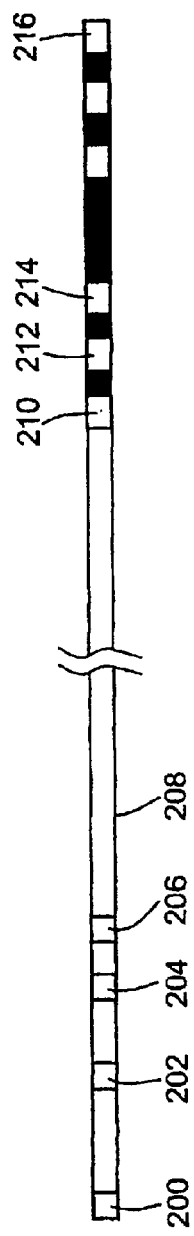
FIG. 2 shows electrodes positioned in the distal region of a guide wire assembly according to a first embodiment of the invention.

FIG. 2 shows a Pressure/volume guide wire assembly according to one embodiment of the invention. Four cylindrical electrodes, 200, 202, 204 and 206 enclosing the guide wire 208 are positioned in the distal region of the guide wire. The electrodes are electrically connected to the connectors 210, 212, 214 and 216 in the proximal end of the guide wire. The male connector in the proximal end could preferably be done according to our U.S. Pat. No. 5,938,624. The electrodes must be electrically insulated from each other in order to obtain correct measurements. This could be achieved for example by covering one or both of the coils 100 and 110 with an insulating material. A conductance measurement is typically performed by applying an alternating current to the outer electrodes 200 and 206. A potential difference can then be measured between electrodes 202 and 204. The potential difference corresponds to the conductance of a substance, e.g. blood and/or tissue, in electrical contact with the electrodes. By certain known assumptions of the electrical properties of e.g. blood and tissue a fairly accurate estimate of a volume, e.g. that of a heart chamber, can be calculated. The volumetric measurement, i.e. the conductance measurement, can by simultaneous pressure measurements provided by the pressure sensor 106, be used to produce Pressure/Volume-loops, considered to be of high diagnostic value.

Figure 3A:
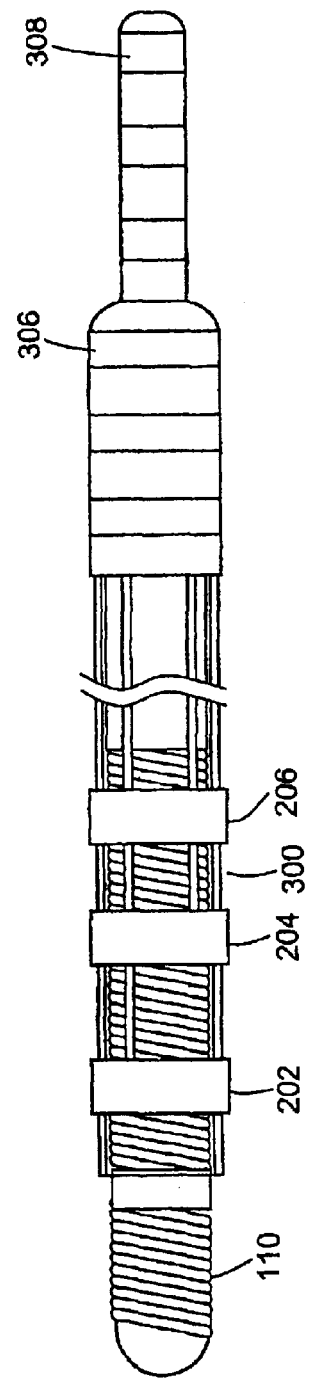
FIG. 3A shows the distal region of according to a second embodiment of the invention and the terminals of the proximal end of the guide wire assembly.
Figure 3B:
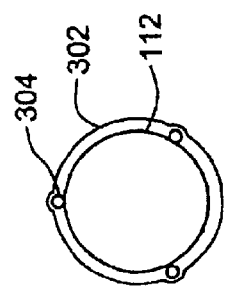
FIG. 3B shows a cross section of the guide wire indicating how electrical leads are positioned outside the proximal tube.

Shown in FIG. 3 is a preferred embodiment of the invention. Here the distal tip 104 and the second coil 110 is used as the first electrode 200. The electrical connection to the proximal end is through the core wire 102 (not shown in FIG. 2), which in this case then extends all through the guide wire. The remaining electrodes 202, 204 and 206 are cylindrical and positioned along the first coil 100 in the distal region. The electrodes need to be electrically insulated from each other, typically achieved by covering the first coil 100 with a thin insulating layer 300. The electrical leads 304 from the electrodes to the proximal end can, as depicted in FIG. 3b run in between the proximal tube 112 and a protective/insulating coating 302. By using the distal tip 104 and the second coil 110 as the first electrode and the core wire 102 as the electrical lead, the construction is significantly simplified. To keep the construction as simple as possible and give parts more than one function is important in order to keep the sensor and guide wire assembly small (diameter 0.035 mm), manufacturing costs low and reduce the risk of malfunction.

For certain applications and in order to effect the electrical properties of the conductance measurement it can be of advantage to not use the entire distal tip 104 and the second coil 110 as the first electrode. Therefore, in an alternative embodiment, part of the distal tip and the second coil is covered with an insulating layer. The insulating layer is arranged to give the electrode, i.e. the uncovered part of the distal tip 104 and the second coil 110, the required dimensions and position. The dimensions could preferably be that of the other electrodes and the position determined by the above considerations. The chosen position could for example be at the distal end of the assembly or at the proximal end of the second coil 110.

In a further embodiment, one of the terminals of the sensor and one of the conductance electrodes can be connected to one and the same electrical lead (signal ground), which eliminates one electrical lead, thereby further simplifying the design.

Figure 4:
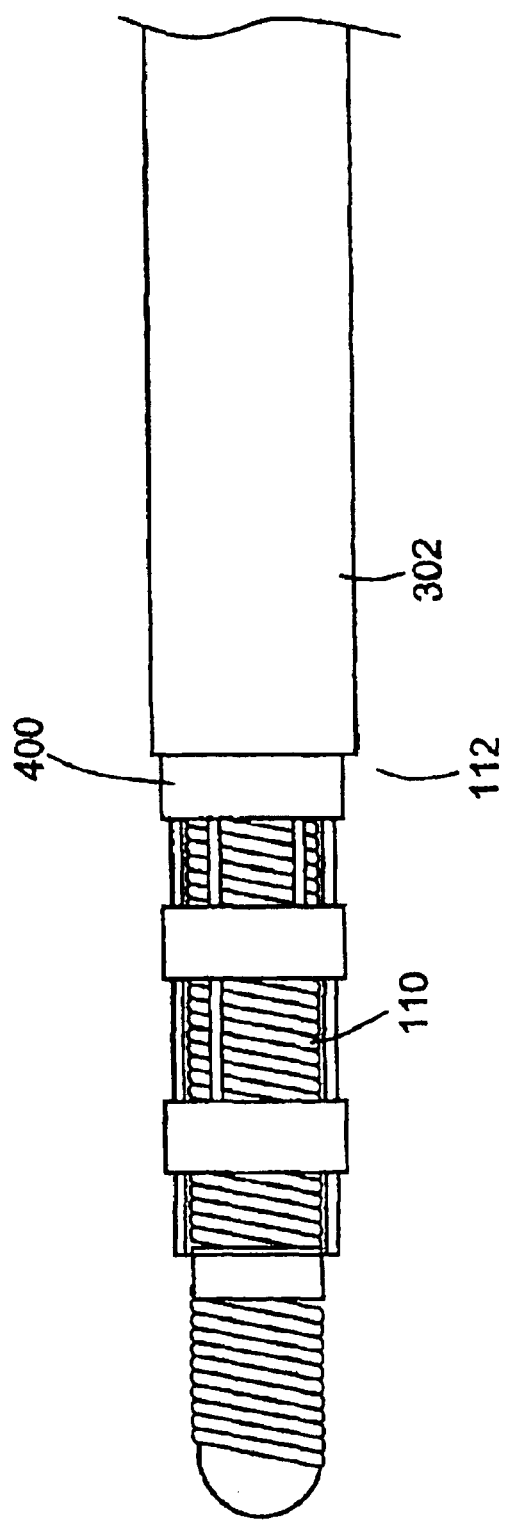
FIG. 4 shows how a portion of the proximal tube is used as an electrode.

A further simplification, according to another embodiment of the invention, is shown in FIG. 4. A portion 400 of the protective/insulating coating 302 of the proximal tube 112 is removed. The size of this portion should be approximately the size of the electrodes 202 or 204, and positioned adjacent to the distal region of the sensor and guide wire assembly. If the proximal tube is made of an electrically conducting material, e.g. stainless steel, the portion 400 can be used as the fourth electrode 206, and the proximal tube itself is used as the electrical lead to the male connector at the proximal end. If both the proximal tube 112 and the core wire 102 are used as electrical leads, they need to be electrically insulated from each other, e.g. by covering the core wire 102 with an insulator. By using this embodiment in combination with the embodiment discuss with reference to FIG. 3 conductance measurements are enabled with a minimum of modifications to the prior art sensor and guide wire assembly. In principle, only two electrodes, 202 and 204, two leads 304, an insulating coating 300, and three new connections in the proximal end needs to be added to the prior art device.

An advantageous feature of the assembly is the use of the proximal tub 112 as one electrical lead, and to use the tube at the very proximal end as one of the contact members 306 of the male connector. This is achieved by simply removing the insulating layer at the distal end to form a preferably circular segment, around the circumference of the tube.

Furthermore, since the core wire 102 is usable as one of the electrical leads, it can also be used for the purpose of providing another contact member 308 of the male connector.

According to one embodiment the electrodes are electrically isolated from each other and the first coil 100 by moulding the electrodes into a plastic material. Alternatively the first coil 100 can be made, at least party, of an insulating material or replaced by a tubular construction of insulating material.

Figure 5:
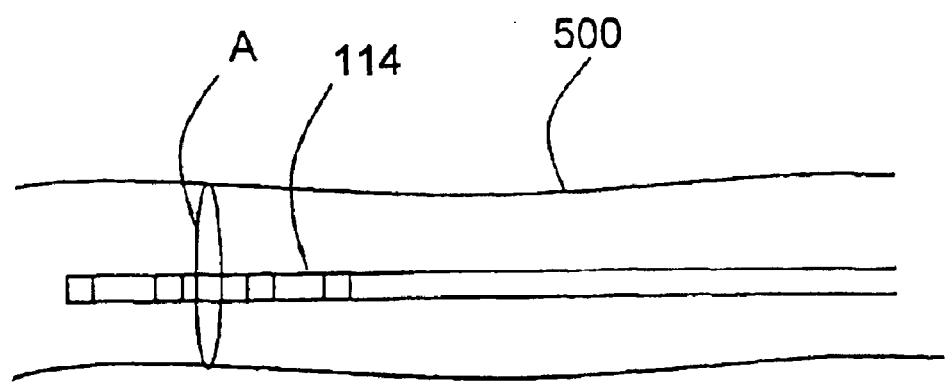
FIG. 5 shows how the guide wire assembly inserted in a blood vessel for a compliance measurement.

In FIG. 5 is shown how a pressure/volume guide wire assembly according to the invention is used for diagnosis of blood vessel functions, e.g. to detect arteriosclerosis. The distal region is positioned within a blood vessel 500. The conductance measurement will in this case correspond to the cross-sectional area A of the vessel. By simultaneously measuring the pressure the compliance of the blood vessel can be observed. To be able to observe the local compliance of a blood vessel will in many cases be helpful in deciding on a appropriate treatment.

The device disclosed above is usable in an inventive way to obtain necessary information to enable characterization of the status of the vascular system of a patient.

Thereby the method comprises introducing a sensor and guide wire assembly into the vascular system, locating it at the desired point of measurement by virtue of the steerablity of the device.

The assembly comprises a pressure sensor and conductance electrodes, preferably four. The assembly is suitably energized and the conductance response to pressure variations is detected in parallel with detection of said pressure variations.

These variations can then be used to calculate e.g. PV loops for the diagnosing of the condition of the heart, or for a calculation of the compliance of a blood vessel, e.g. to determine whether or not arteriosclerosis is at hand.

Additional advantages and modifications will readily be appreciated by those skilled in the art. Therefore, the invention in its broader aspects is not limited to the specific details, and representative devices, shown and described herein. Accordingly, various modifications may be made without departing from the spirit or scope of the general inventive concept as defined by the appended claims.

What is claimed is:

1. A sensor and guide wire assembly having a distal end and a proximal end comprising:
   a core wire having a distal end and a proximal end;
   a sensor mounted in the distal end region of said core wire;
   a tube enclosing said core wire over at least a fraction of a length of said core wire such that said core wire extends out from a distal end of said tube;
   a first enclosure arranged to enclose a first portion of said core wire extending out from said distal end of said tube, said first enclosure being located nearer to said proximal end of said core wire than said sensor;
   a second enclosure arranged to enclose a second portion of said core wire extending out from said distal end of said tube, said second enclosure being located nearer to said distal end of said core wire than said sensor; wherein
   said guide wire further comprises at least two electrodes for conductance measurement, and said at least two electrodes are electrically insulated from each other.

2. Sensor and guide wire assembly according to claim 1, wherein said first enclosure is a first coil and said second enclosure is a second coil.

3. Sensor and guide wire assembly according to claim 2, wherein said second coil or a portion thereof is used as a first of said at least two electrodes.

4. Sensor and guide wire assembly according to claim 1, wherein said first of said at least two electrodes utilises said core wire as electrical connection to the proximal end of the guide wire.

5. Sensor and guide wire assembly according to claim 1, wherein the number of electrodes for conductance measurement is four.

6. Sensor and guide wire assembly according to claim 1, wherein at least one, and preferably two of said electrodes are cylindrical and enclose said guide wire.

7. Sensor and guide wire assembly according to claim 1, wherein said tube is made of electrically conducting material and for a larger first portion covered with an insulating material; and
   said conducting material of said tube is exposed over a smaller second portion and is utilised as the second of said at least two electrodes.

8. Sensor and guide wire assembly according to claim 7, wherein said second of said at least two electrodes utilises said first portion of said tube as electrical connection to the proximal end of the guide wire.

9. Sensor and guide wire assembly according to claim 1, wherein said sensor is a pressure sensor.

10. A sensor and guide wire assembly comprising:
    a pressure sensor having a plurality of terminals, the sensor being mounted in a distal end region of said guide wire;
    at least two electrodes for conductance measurement provided in the distal end region of said guide wire and wherein said at least two electrodes are electrically insulated from each other; wherein one of said sensor terminals and one of said conductance electrodes are connected to a common electrical lead.

11. Sensor and guide wire assembly according to claim 10, wherein the number of electrodes for conductance measurement is four.

12. A sensor and guide wire assembly comprising:
    a pressure sensor having a plurality of terminals, the sensor being mounted in a distal end region of said guide wire;
    at least two electrodes for conductance measurement provided in the distal end region of said guide wire and said at least two electrodes are electrically insulated from each other; and
    wherein the guide wire includes:
    a core wire having a distal end and a proximal end; and
    a tube enclosing said core wire over at least a fraction of a length of said core wire such that said core wire extends out from a distal end of said tube, and said core wire and said tube respectively being used as electrical leads.

13. Sensor and guide wire assembly according to claim 12, wherein the number of electrodes for conductance measurement is four.

* * * * *